US00PP33138P3

(12) United States Plant Patent
Mazzardis

(10) Patent No.: US PP33,138 P3
(45) Date of Patent: Jun. 8, 2021

(54) BLUEBERRY PLANT NAMED 'NS 15-13'

(50) Latin Name: ***Vaccinium* hybrid**
Varietal Denomination: NS 15-13

(71) Applicant: Next Progeny Pty., Ltd., Subiaco (AU)

(72) Inventor: Vincent David Andrew Mazzardis, Joondalup (AU)

(73) Assignee: Next Progeny Pty., Ltd., Subiaco (AU)

( * ) Notice: Subject to any disclaimer, the term of this patent is extended or adjusted under 35 U.S.C. 154(b) by 0 days.

(21) Appl. No.: 16/990,818

(22) Filed: Aug. 11, 2020

(65) Prior Publication Data

US 2021/0051826 P1 Feb. 18, 2021

(30) Foreign Application Priority Data

Aug. 15, 2019 (QZ) ..... PBR 2019/1982

(51) Int. Cl.
*A01H 6/36* (2018.01)
*A01H 5/00* (2018.01)

(52) U.S. Cl.
USPC ..... Plt./157
CPC ..... *A01H 6/368* (2018.05)

(58) Field of Classification Search
USPC ..... Plt./157
See application file for complete search history.

*Primary Examiner* — Annette H Para
(74) *Attorney, Agent, or Firm* — Randall Danskin, P.S.

(57) ABSTRACT

A new and distinct variety of blueberry plant, which is denominated varietally as 'NS 15-13' is described and which produces fruit considered large, low to medium in acidity, and medium to firm under the ecological conditions prevailing in Yanchep, Western Australia.

2 Drawing Sheets

Latin name: *Vaccinium* hybrid.

Variety denomination: The invention relates to a new, novel, and distinct variety of blueberry plant, a *Vaccinium* hybrid, with a variety denomination hereinafter as 'NS 15-13'.

CROSS REFERENCE TO RELATED APPLICATIONS

This application claims the benefit of priority under 35 USC § 119 to Community Plant Variety Office (CPVO) Application No. 2019/1982 for Community Plant Variety Rights, filed on Aug. 15, 2019 for a blueberry plant with a variety denomination of 'NS 15-13', which is herein incorporated by reference in its entirety.

SUMMARY

The new variety of blueberry plant resulted from an ongoing development program of plant breeding conducted to identify such plants. The purpose of the program was to improve the commercial quality of blueberry plants and other plant species. To this end, controlled, hybrid, cross-pollinations were made in order to produce plant populations from which improved progeny were evaluated and thereafter selected.

The 'NS 15-13' blueberry plant was originated and selected from a population of new plants growing on the breeder's property, which is located at Yanchep Springs in Yanchep, Western Australia. The new variety of blueberry plant was derived from a controlled, hybrid, cross-pollination of the seed parent, blueberry plant 'EB 9-4' (U.S. Plant Pat. No. 28,334), and a pollen parent, blueberry plant 'EB 8-46' (U.S. Plant Pat. No. 26,173) during the 2013 growing season.

PRIOR VARIETIES

The seed parent 'EB 9-4' is characterized principally by a semi-upright to intermediate growth habit, a medium vigor, a very early season first pick date, and further produces large- to very-large-sized, firm, high sweetness, and low to medium acidity fruit under the ecological conditions occurring in Yanchep, Western Australia. Also, the seed parent 'EB 9-4' exhibits a very early date of bloom time and a last pick date in February of the following year under the ecological conditions occurring in Yanchep, Western Australia. Further, the seed parent 'EB 9-4' is evergreen and produces fruit on one-year-old and current season's shoots.

The pollen parent 'EB 8-46', on the other hand, is characterized principally by an intermediate growth habit, a medium to strong vigor, an early season first pick date, and further produces very-large-sized, firm to very firm, high sweetness, and low acidity fruit under the ecological conditions occurring in Yanchep, Western Australia. Also, the pollen parent 'EB 8-46' exhibits an early date of bloom time and a November last pick date under the ecological conditions occurring in Yanchep, Western Australia. Further, the pollen parent 'EB 8-46' is semi-evergreen and produces fruit on one-year-old and current season's shoots.

ORIGIN

The seed from the seed parent 'EB 9-4' produced approximately 2,400 plants following cross-pollination. These new plants were then grown at the aforementioned property, and fruit from these new plants was first observed in 2014. A subsequent assessment of these same self-fertile, new plants conducted during the 2015 growing season led to selecting the 'NS 15-13' variety for further evaluation.

ASEXUAL REPRODUCTION

The further evaluation included an asexual vegetative propagation, by vegetative cuttings, at Yanchep Springs in Yanchep, Western Australia. Subsequent evaluations of the newly derived plants in the 2016 growing season led to a conclusion that the 'NS 15-13' variety was a distinct and new variety of blueberry plant found to be true to the original plant. The new variety of blueberry plant was considered to be novel in view of its large and medium to firm fruit, which exhibited low to medium acidity.

COMPARISONS

In comparison to the seed parent 'EB 9-4' under the ecological conditions occurring in Yanchep, Western Australia, the new variety has noteworthy fruit. In this regard, the seed parent produces fruit considered to be large to very large in size. However, the new variety of blueberry plant produces fruit considered to be large in size. In addition, both the seed parent and the new variety produce fruit considered to be low to medium in acidity. Further, the seed parent produces fruit considered to be firm. This is in contrast to the fruit of the new variety of blueberry plant, which is considered to be medium to firm.

In comparison to the pollen parent 'EB 8-46' under the ecological conditions occurring in Yanchep, Western Australia, the new variety has noteworthy fruit. In this regard, the pollen parent produces fruit considered to be very large in size. However, the new variety of blueberry plant produces fruit considered to be large in size. In addition, the pollen parent produces fruit considered to be low in acidity. In contrast, the new variety produces fruit considered to be low to medium in acidity. Further, the pollen parent produces fruit considered to be firm to very firm. This is in contrast to the fruit of the new variety of blueberry plant, which is considered to be medium to firm.

The new variety of blueberry plant is readily distinguishable from the most closely related, known variety, 'EB 8-46', the pollen parent.

The comparisons described above are summarized in Table 1 below.

TABLE 1

Summary of Comparisons

| | 'NS 15-13' | 'EB 9-4' (Seed) | 'EB 8-46' (Pollen) |
|---|---|---|---|
| Fruit size | Large | Large to very large | Very large |
| Fruit acidity | Low to medium | Low to medium | Low |
| Fruit firmness | Medium to firm | Firm | Firm to very firm |

In addition, Table 2 below compares the 'NS 15-13' variety to several sibling cultivars that resulted from same the seed parent 'EB 9-4' and pollen parent 'EB 8-46', namely, 'NS 15-5' (U.S. Plant patent application Ser. No. 17/087,369), 'NS 15-22' (U.S. Plant patent application Ser. No. 16/991,651), and 'NS 16-15' (U.S. Plant patent application Ser. No. 16/991,868).

TABLE 2

Comparison to Sibling Cultivars

| | 'NS 15-13' | 'NS 15-5' | 'NS 15-22' | 'NS 16-15' |
|---|---|---|---|---|
| Fruit size | Large | Large to very large | Large to very large | Large |

TABLE 2-continued

Comparison to Sibling Cultivars

| | 'NS 15-13' | 'NS 15-5' | 'NS 15-22' | 'NS 16-15' |
|---|---|---|---|---|
| Fruit acidity | Low to medium | Very low to low | Low | Low |
| Fruit firmness | Medium to firm | Medium | Medium | Firm |
| Plant vigor | Medium to strong | Strong | Strong | Medium to strong |
| Fruit cluster density | Sparse to medium | Medium to dense | Medium | Dense |
| Fruiting type | on one-yr-old shoots only | on one-yr-old and current season's shoots | on one-yr-old shoots only | on one-yr-old shoots only |
| Vegetative bud burst timing | Early, end of May | Early, end of May | Early, end of May | Early, mid-Jun |
| Fruit sweetness | Medium | Medium | Medium | Medium |

BRIEF DESCRIPTION OF THE DRAWINGS

The accompanying drawings are color photographs of the new blueberry plant 'NS 15-13' during the third year of growth under the ecological conditions prevailing at the breeder's property, which is located at Yanchep Springs in Yanchep, Western Australia.

Figure 1:
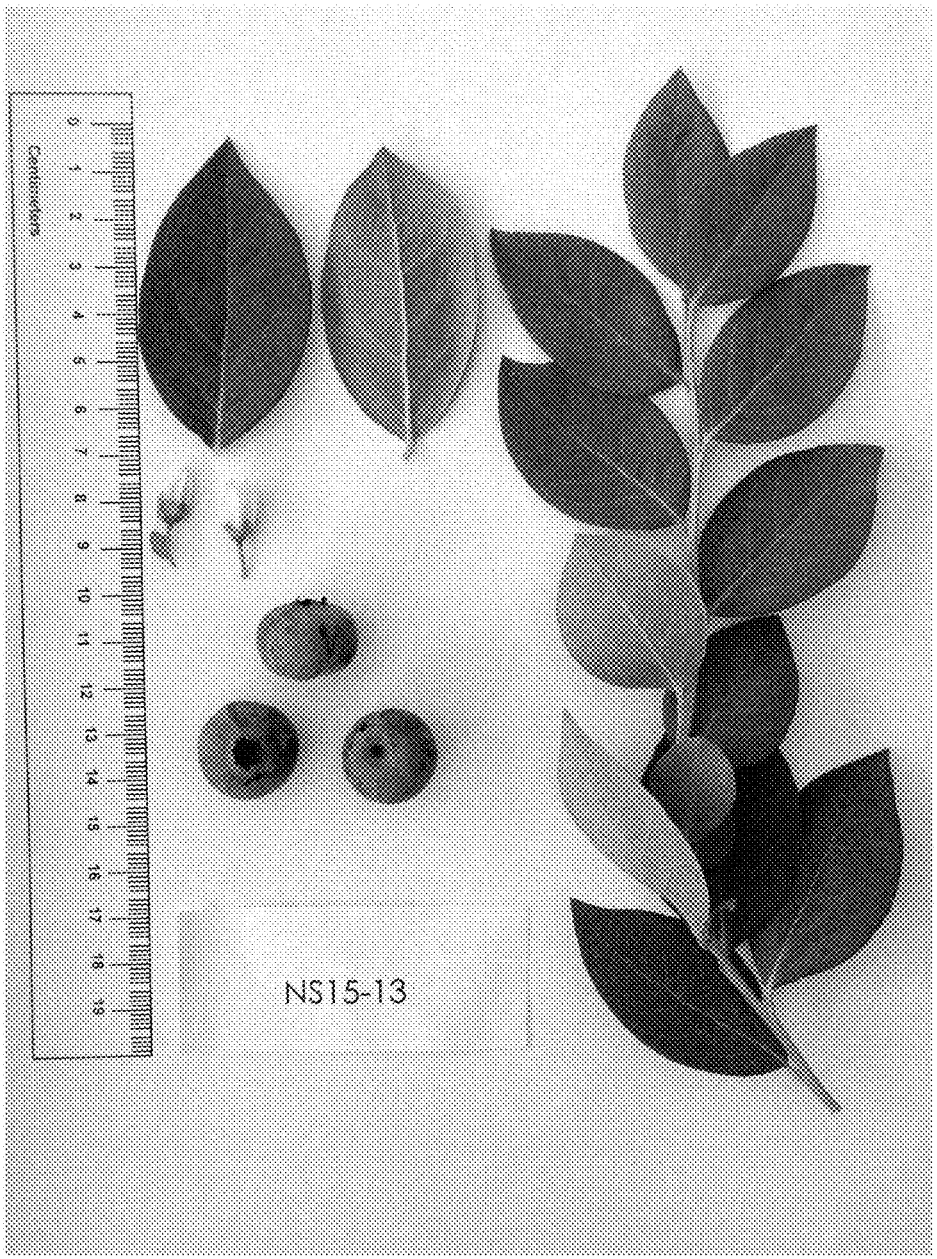
FIG. 1 is a color photograph, which shows fruit, blooms, leaves, and a portion of a vegetative stem of the new blueberry plant 'NS 15-13', the fruit being sufficiently mature for harvesting and shipment. This photograph also depicts the large fruit size and the color of the ripe fruit, two leaves showing the sizes and the upper and under side colorations thereof, two blooms at different stages of maturation, and additional leaves on the stem at different stages of maturation.
Figure 2:
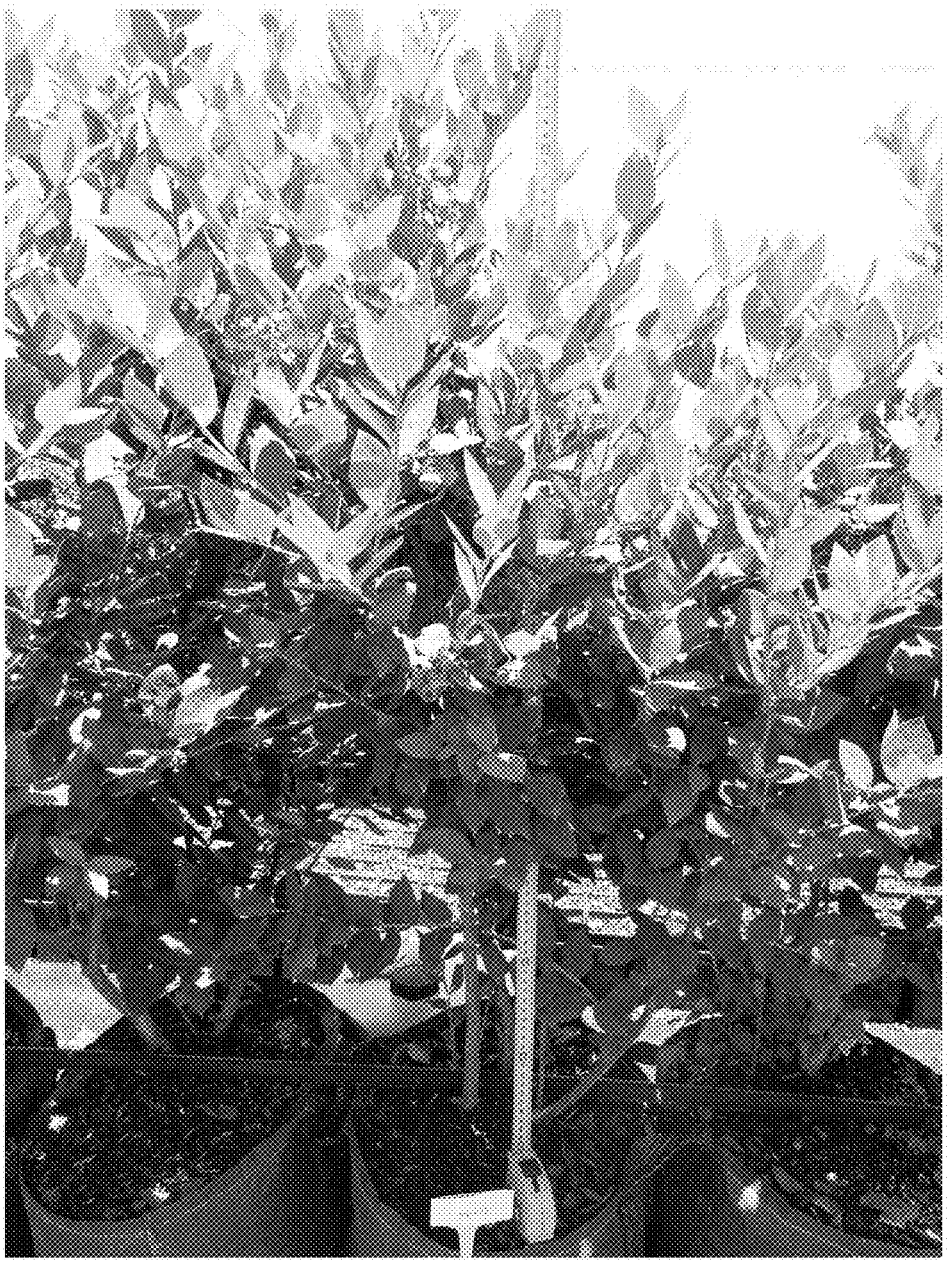
FIG. 2 is a color photograph, which shows the new blueberry plant 'NS 15-13'. This photograph depicts a mature bush with ripe and unripe fruits, the large fruit size, and the upright growth habit of the bush. The ripe fruit is sufficiently mature for harvesting and shipment.

The colors in these photographs are as nearly true as is reasonably possible in a color representation of this type. Due to variations in color printers and/or chemical development, processing and printing, the colors of the plant parts depicted in these photographs may, or may not, be accurate when compared to the actual specimen. For this reason, color references are made to the color plates (Royal Horticultural Society Colour Chart, Sixth Edition, hereinafter, "R.H.S.") and descriptions provided.

DETAILED BOTANICAL DESCRIPTION

Not A Commercial Warranty

The following detailed description was prepared solely to comply with the provisions of 35 U.S.C. § 112, and does not constitute a commercial warranty (either expressed or implied) that the present variety will, in the future, display the botanical, horticultural, or other characteristics set forth herein. Therefore, this disclosure may not be relied upon to support any future legal claims including, but not limited to, breach of warranty of merchantability, or fitness for any particular purpose, or non-infringement, which is directed in whole, or in part, to the present new variety of plant.

Referring more specifically to the botanical features of this new and distinct variety of blueberry plant, the following has been observed during the third year of growth under the ecological conditions prevailing at the breeder's property, which is located at Yanchep Springs in Yanchep, Western Australia.

Plant: General.

*Vigor*.—Considered medium to strong for the species.

*Growth habit*.—Considered upright. This is in comparison to the commercial variety 'Ivanhoe' (unpatented), which is considered to be upright.

*Average size of plant*.—1.3 meters in height by 0.80 meters in width.

*Internode length* (*space between nodes*).—Considered short to medium, 15.7 millimeters (mm).

*Bark color*.—RHS Light Brownish Grey Group 201B.

*Color, one year old shoots*.—RHS Light Yellow Green Group 145B.

*Fruiting type*.—On one-year-old shoots only, in like manner to commercial varieties 'Darrow' (unpatented) and 'Patriot' (unpatented).

Foliage: General.

*Average leaf length*.—Considered medium for the species, 56.9 mm.

*Average leaf width*.—Considered medium for the species, 27.9 mm.

*Color of leaf upper*.—RHS Moderate Yellow Green Group 137C.

*Color of leaf underside*.—RHS Moderate Yellow Green Group 139C.

*Vein color of plant leaf*.—RHS Light Yellow Green Group 145C.

*Venation pattern of leaf*.—Pinnate reticulate.

*Leaf apex texture*.—Glabrous.

*Leaf apex shape*.—Acute.

*Leaf base shape*.—Acute.

*Leaf shape*.—Elliptic.

*Leaf margin*.—Entire.

*Leaf arrangement of plant*.—Alternate.

*Petiole length*.—3.42 mm.

*Petiole diameter*.—1.86 mm.

*Petiole color*.—RHS Light Yellow Green 145C.

Flowers:

*Number of flowers/inflorescence*.—4 to 5.

*Length of inflorescence* (*excluding pedicel*).—Considered medium, 5.29 mm.

*Corolla shape*.—Urceolate.

*Corolla tube surface texture*.—Ridges are present on the corolla tube.

*Average corolla length*.—12.08 mm.

*Corolla diameter*.—9.81 mm.

*Corolla aperture size*.—6.17 mm.

*Corolla color*.—RHS White Group NN155B.

*Pedicel color*.—RHS Moderate Yellow Green Group 143D.

*Pedicel length*.—8.18 mm.

*Average calyx diameter*.—4.29 mm.

*Average calyx basin depth*.—Considered medium, 1.44 mm.

*Attitude of sepals*.—Erect.

*Type of sepals*.—Straight.

Reproductive organs:

*Size of pollen anthers*.—5.12 mm.

*Color of pollen anthers*.—RHS Brownish Orange Group N167B.

*Pistil length*.—9.08 mm.

*Pistil color*.—RHS Light Yellow Green Group 145C.

Fruit:

*Color of unripe fruit*.—RHS Strong Yellowish Green Group N144A.

*Color of fruit skin*.—RHS Bluish Black Group 203C, also considered "dark blue" in like color to the commercial variety 'Heerma' (unpatented), after removal of bloom.

*Color of ripe fruit flesh*.—RHS Light Yellow Green Group 145C.

*Color of seeds*.—RHS Moderate Reddish Brown Group 176B.

*Average fruit size*.—19 mm in diameter and 13.99 mm in height.

*Average weight of fruit*.—3.37 grams.

*Berry shape*.—Considered oblate.

*Sweetness when ripe*.—Considered medium to high for the species.

*Firmness when ripe*.—Considered medium to firm for the species. This is in contrast to the seed parent 'EB 9-4', wherein the firmness is considered firm, and the pollen parent 'EB 8-46', wherein the firmness is considered firm to very firm.

*Acidity when ripe*.—Considered low to medium for the species. This is comparable to the seed parent 'EB 9-4', wherein the fruit acidity is also considered low to medium. This is in contrast to the pollen parent 'EB 8-46', wherein the fruit acidity is considered low.

*Cluster density*.—Considered sparse to medium dense for the species.

*Average fruit production*.—3.5 kilograms on a two-year-old bush.

*Storability of fruit*.—Considered excellent for the species.

*Market use of fruit*.—1st grade fresh market fruit.

*Date of bud burst*.—This variety is evergreen under the ecological conditions prevailing in Yanchep, Western Australia, but a bud break occurs the end of May, which is considered early for the species.

*Date of bloom time*.—This variety is evergreen under the ecological conditions prevailing in Yanchep, Western Australia, but a bloom time occurs in early July, which is considered very early on one-year old shoot in like manner to the commercial variety 'Patriot' (unpatented).

*Duration of bloom time*.—6 weeks.

*Beginning of fruit ripening*.—considered very early on one-year-old shoot in like manner to the commercial variety 'Bluetta' (unpatented).

*First pick date*.—The observed date of the first pick is approximately September under the ecological conditions prevailing in Yanchep, Western Australia.

*Last pick date*.—The observed date of the last pick is approximately November under the ecological conditions prevailing in Yanchep, Western Australia.

*Pollination requirements*.—Self-fertile.

*Resistance to pests and disease*.—No particular resistance noted. The variety has not been tested to detect any resistance.

Although the new variety of blueberry plant possesses the described characteristics when grown under the ecological conditions prevailing in Yanchep, Western Australia, it should be understood that variations are to be expected in the usual magnitude and characteristics incident to changes in growing conditions, fertilization, pruning, pest control, frost, climatic variables, and horticultural management.

Having thus described and illustrated a new variety of blueberry plant, what is claimed to secure a plant Letters Patent is:

1. A new and distinct variety of blueberry plant, substantially as illustrated and described, which is characterized principally as to novelty by producing fruit considered large, low to medium in acidity, and medium to firm under the ecological conditions prevailing in Yanchep, Western Australia.

* * * * *